(12) United States Patent
Kaneda et al.

(10) Patent No.: US 8,999,126 B2
(45) Date of Patent: Apr. 7, 2015

(54) LACTATE SENSOR (71) Applicant: ARKRAY, Inc., Kyoto-shi (JP)

(72) Inventors: Hisashi Kaneda, Kyoto (JP); Takehiro Yamaguchi, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 137 days.

(21) Appl. No.: 13/625,250

(22) Filed: Sep. 24, 2012

(65) Prior Publication Data

US 2013/0075277 A1 Mar. 28, 2013

(30) Foreign Application Priority Data

Sep. 26, 2011 (JP) ................................ 2011-209459
Sep. 19, 2012 (JP) ................................ 2012-206151

(51) Int. Cl.
*G01N 27/327* (2006.01)
*C12Q 1/26* (2006.01)
*C12Q 1/00* (2006.01)

(52) U.S. Cl.
CPC ............ *G01N 27/3272* (2013.01); *C12Q 1/005* (2013.01); *C12Q 1/004* (2013.01); *C12Q 1/26* (2013.01); *G01N 2333/904* (2013.01)

(58) Field of Classification Search
CPC ..... G01N 27/3271; C12Q 1/004; C12Q 1/005
See application file for complete search history.

(56) References Cited

U.S. PATENT DOCUMENTS

| 5,288,636 | A | * | 2/1994 | Pollmann et al. ......... 204/403.14 |
| 5,720,862 | A |   | 2/1998 | Hamamoto et al. |
| 2007/0031913 | A1 | * | 2/2007 | Kimura ......................... 435/23 |
| 2007/0034512 | A1 | * | 2/2007 | Yamaoka et al. ........ 204/403.01 |
| 2007/0080073 | A1 | * | 4/2007 | Wu et al. ..................... 205/777.5 |
| 2008/0073207 | A1 | * | 3/2008 | Teodorczyk et al. .... 204/403.14 |

FOREIGN PATENT DOCUMENTS

| CN | 1875265 A | 12/2006 |
| EP | 1324038 A2 | 7/2003 |
| EP | 1679508 A1 | 7/2006 |
| EP | 2474825 A1 | 7/2012 |
| JP | 3498105 B2 | 12/2003 |
| JP | 4088312 B2 | 2/2008 |
| WO | 99/13100 A1 | 3/1999 |
| WO | WO-2005/043146 A1 | 5/2005 |

OTHER PUBLICATIONS

"Lactate Oxidase", Sep. 14, 2010, pp. 189-192, XP002689981.

* cited by examiner

*Primary Examiner* — Alexander Noguerola
(74) *Attorney, Agent, or Firm* — Fox Rothschild LLP (57) ABSTRACT

A lactate sensor capable of accurately measuring a lactate concentration in a short period of time. The lactate sensor includes an insulating substrate, an electrode system including at least a working electrode and a counter electrode provided on the substrate, and a reagent layer provided on the electrode system. The reagent layer contains lactate oxidase, it mediator, and N-(2-acetamide)-2-aminoethanesulfonic acid.

10 Claims, 5 Drawing Sheets

LACTATE SENSOR

BACKGROUND OF THE INVENTION

1. Field of the Invention

The present disclosure relates to a lactate sensor containing lactate oxidase and a mediator.

2. Description of Related Art

It is known that lactate is a fatigue substance produced in the body after exercise. Accordingly, lactate sensors are widely used at training fields or training sites to check the effect of training or the state of training. Meanwhile, it is required that lactate sensors enable easy detection/measurement. However, because the per-unit cost of lactate oxidase used for lactate sensors is higher than that of glucose oxidase used for glucose sensors, lactate oxidase is problematic in that it results in a high sensor cost. In this regard, in order to address this problem, for example, a lactate sensor that contains phosphate in a reaction layer to enhance lactate oxidase activity has been proposed (Japanese Patent No. 3498105).

In addition, there is a method for producing a biosensor such as a lactate sensor, for example, a method that includes the step of forming an inorganic gel layer containing at least a mediator, a surfactant, a buffer, and a layered inorganic compound on the surface of a substrate that has electrodes (Japanese Patent No. 4088312).

SUMMARY OF THE INVENTION

As described above, because lactate serves as a marker indicating the level of fatigue, lactate sensors are widely used in, for example sports training. Meanwhile, in training, it is necessary to promptly measure and check the level of fatigue in order to determine the load of subsequent exercise. Therefore, a lactate sensor that is capable of carrying out an accurate measurement in a short period of time is required. However, because the rate of enzyme reaction in conventional lactate sensors is low and thus measurements take a long period of time, a further reduction of the measurement time is required.

Accordingly, the present disclosure, as one aspect, is to provide a lactate sensor capable of accurately measuring the lactate concentration in a short period of time.

The present disclosure, as one aspect, relates to a lactate sensor (hereinafter also referred to as a "lactate sensor of the present disclosure") including an insulating substrate, an electrode system including at least a working electrode and a counter electrode, provided on the substrate, and a reagent layer provided on the electrode system, and the reagent layer contains lactate oxidase, a mediator % and N-(2-acetamide)-2-aminoethanesulfonic acid (hereinafter also referred to as "ACES").

The present disclosure, as another aspect, relates to a method for measuring a lactate concentration (hereinafter also referred to as it "lactate concentration measurement method of the present disclosure"), including bringing a sample into contact with a reagent containing lactate oxidase and N-(2-acetamide)-2-aminoethanesulfonic acid, and electrochemically measuring a reaction between lactate in the sample and the lactate oxidase via a mediator.

The present disclosure, as still another aspect, relates to a method for producing a lactate sensor (hereinafter also referred to as a "production method of the present disclosure"), including forming a reagent layer containing lactate oxidase, a mediator, and N-(2-acetamide)-2-aminoethanesulfonic acid on an electrode system provided on an insulating substrate, the electrode system including at least a working electrode and a counter electrode.

According to the present disclosure, as one aspect, a lactate sensor capable of accurately measuring the lactate concentration in a short period of time can be provided.

DETAILED DESCRIPTION OF THE INVENTION

The present disclosure, in one aspect, is based on the findings that, with conventional lactate sensors, the rate of enzymatic reaction is low, and it is thus not possible to attain sufficient sensitivity in a short-time measurement particularly when the sample has a high lactate concentration. Also, the present disclosure, in another aspect, is based on the findings that use of ACES as a buffer makes it possible to enhance the rate of enzymatic reaction of lactate oxidase, and it is thus possible to shorten the time needed for the reaction and accurately measure the lactate concentration in a short period of time, preferably even when the sample has a high lactate concentration.

Without being limited by any particular mechanism, it is presumed that ACES enhances the lactate oxidase activity and the rate of reaction between lactate in a sample and lactate oxidase is thereby enhanced. Therefore, it seems that the time from the beginning to the end of the enzymatic reaction is shortened, thus making it possible that the duration of the reaction is shortened and also that the lactate concentration is accurately measured in a short period of time even when a sample has a high lactate concentration. Note that these mechanisms should not be construed as limiting the present disclosure. Herein, the phrase "when a sample has a high lactate concentration" in one or a plurality of embodiments refers to a lactate concentration in a sample of 10 mmol/L or more, 12 mmol/L or more, or 20 mmol/L or more.

[Sample]

The measurement sample for the lactate sensor and the lactate concentration measurement method of the present disclosure in one or a plurality of embodiments may be a biological sample such as blood, body fluid, or urine, or may be another liquid sample.

[Lactate Sensor]

The lactate sensor of the present disclosure is configured with an insulating substrate, an electrode system including at least a working electrode and a counter electrode, and a reagent layer, the electrode system is provided on the substrate, and the reagent layer is provided on the electrode system.

It is sufficient that, in one or a plurality of embodiments, the electrode system includes at least a working electrode and a counter electrode, and the electrode system may further include a reference electrode or the like. The electrodes are not particularly limited, and electrodes that are used in conventional biosensors or biosensors that may be developed in the future, such as lactate sensors, and glucose sensors, can be used. Neither the working electrode nor the counter electrode is particularly limited, and in one or a plurality of embodiments, carbon electrodes or metal electrodes may be used. In one or a plurality of embodiments, carbon may be pyrolytic graphite carbon, glassy carbon, carbon paste, perfluorocarbon (PFC), or the like. In one or a plurality of embodiments, metal may be platinum, gold, silver, nickel, palladium, or the like. The reference electrode is not particularly limited, and electrodes generally used in electrochemical experiments can be used, and in one or a plurality of embodiments, the reference electrode may be a saturated calomel electrode, a silver-silver chloride electrode, or the like. The electrode system is not particularly limited and can be formed by a known method in accordance with the materials of the electrodes to be formed, and in one or a plurality of embodiments, the electrode system can be formed by photolithography vapor deposition, sputtering, printing, or the like. In one or a plurality of embodiments, printing may be screen printing, gravure printing, flexographic printing, or the like.

The material of the insulating substrate is not particularly limited, and materials that are used for conventional biosensors or biosensors that may be developed in the future can be used, and in one or a plurality of embodiments, the material may be silicon, glass, glass epoxy ceramic, polyethylene terephthalate (PET), polystyrene, polymethacrylate, polypropylene, acrylic resin, polyvinyl chloride, polyethylene, polypropylene, polyester, polyimide, or the like.

In the lactate sensor of the present disclosure, the reagent layer contains lactate oxidase, a mediator, and ACES.

Lactate oxidase is not particularly limited, and known lactate oxidase and commercially available lactate oxidase that are used in conventional lactate sensors or lactate sensors that may be developed in the future can be used. The content of lactate oxidase per one lactate sensor in one or a Plurality of embodiments may be the amount found in conventional lactate sensors or lactate sensors that may be developed in the future, and from the viewpoint, of maintaining productivity (cost) and detection sensitivity it is preferably 1.0 to 3.0 U, 1.6 to 2.4 U, or 1.8 to 2.2 U. Herein, the character "U" refers to an enzyme unit, and 1 U corresponds to the amount of enzyme with which lactate oxidase oxidizes 1 µmol of lactate in 1 minute at 30° C.

Herein, the phrase "the content per one lactate sensor" in one or a plurality of embodiments refers to the amount used in a lactate sensor having one electrode system that includes at least a working electrode and a counter electrode, in one or a plurality of other embodiments it refers to the amount contained in the reagent layer provided on one electrode system, and in one or a plurality of other embodiments, it refers to the amount provided so as to be contained, in a reaction system formed by dissolution of the reagent layer caused by a sample when the sample is introduced (when the lactate sensor is used). Also, herein, the lactate sensor as used in the phrase "the content per one lactate sensor" in one or a plurality of embodiments refers to a lactate sensor of a conventional size that is used on a blood sample and to which a blood sample is added in an amount of, for example, 0.1 to 5.0 µl or 0.3 to 1.0 µl. Also, the lactate sensor in one or a plurality of other embodiments refers to a lactate sensor in which the volume of the reaction system farmed by a contact between a blood sample and the reagent layer is, for example, 0.1 to 5.0 µl or 0.3 to 1.0 µl. Therefore, the "content per one lactate sensor" in one or a plurality of embodiments can be suitably adjusted so as to be within the range disclosed herein in accordance with the number of electrode systems and/or the volume of a sample or reaction system.

ACES (N-(2-acetamide)-2-aminoethanesulfonic acid, $C_4H_{10}N_2O_4S$) is a Good's buffer, and commercially available ACES can be used. The content of ACES per one lactate sensor in one or a plurality of embodiments is, for example, 0.1 to 10 wt % or 0.5 to 5.0 wt % from the viewpoint of shortening the measurement time and enhancing measurement sensitivity. The ratio of the ACES to the entire reagent solution for preparing a reagent layer of one lactate sensor in one or a plurality of embodiments is, for example, 0.1 to 10 wt % or 0.5 to 5.0 wt % from the viewpoint, of shortening the measurement time and enhancing measurement sensitivity. The lactate sensor of the present disclosure may contain a buffer other than ACES. In one or a plurality of embodiments, from the viewpoint, of shortening the measurement time and enhancing measurement sensitivity it is preferable that the proportion of ACES in the entire buffer is 50 wt % or more or 80 wt % or more, or the entire buffer is substantially composed of ACES.

The mediator in one or a plurality of embodiments may be potassium ferricyanide, cytochrome C, pyrroloquinoline quinone (PQQ), NAD+, NADP+, a copper complex, a ruthenium compound, phenazine methosulfate or a derivative thereof, or the like. These compounds may be used singly and two or more may be used as a combination. Among these compounds, from the viewpoint of shortening the measurement time and enhancing measurement sensitivity it is preferable to use a ruthenium compound or a combination of a ruthenium compound and phenazine methosulfate or a derivative thereof.

Usable ruthenium compounds are those that have been used or that may be used in the future as mediators for biosensors. In one or a plurality of embodiments, it is preferable that the ruthenium compound is capable of existing in the reaction system as an oxidized ruthenium complex. Regarding the ruthenium complex, in one or a plurality of embodiments, the ligand thereof is not particularly limited as long as the ruthenium complex functions as a mediator (electron carrier), and it is preferable to use an oxidized ruthenium complex represented by the chemical formula below:

$$[Ru(NH_3)_5X]^{n+}$$

wherein X in one or a plurality of embodiments may be $NH_3$, a halogen ion, CN, pyridine, nicotinamide, or $H_2O$, with $NH_3$ or a halogen ion (for example, $Cl^-$, $F^-$, $Br^-$, or $I^-$) being particularly preferable. The symbol "n+" in the chemical formula above indicates the valency of the oxidized ruthenium (III) complex, and is suitably determined according to X.

The content of ruthenium compound per one lactate sensor in one or a plurality of embodiments from the viewpoint of productivity (cost) and detection sensitivity is preferably 0.1 to 100 µg, to 1 to 80 µg, or 10 to 50 µg.

Phenazine methosulfate and derivatives thereof (hereinafter also referred to as "PMS") in one or a plurality of embodiments may be phenazine methosulfate, 1-methoxy-5-methyl phenazinium methyl sulfite (1-methoxy PMS), and the like. From the viewpoint, of reagent stability 1-methoxy PMS is preferable.

The content of PMS per one lactate sensor in one or a plurality of embodiments from the viewpoint of productivity (cost) and detection sensitivity is preferably 1 to 2000 pmol, 10 to 1000 pmol, or 100 to 500 pmol.

It is preferable that the reagent layer in one or a plurality of embodiments contains a polysaccharide and/or an oligosaccharide (hereinafter also collectively referred to as a "sugar") from the viewpoint of further enhancing measurement sensitivity. Herein, the term "polysaccharide" refers to a sugar in which ten or more monosaccharides are bonded, and in one or a plurality of embodiments, the polysaccharide may be dextran, cyclodextran, dextrin, starch, cellulose, agarose, or the like. Herein, the term "oligosaccharide" refers to a sugar in which fewer than ten monosaccharides are bonded, and in one or a plurality of embodiments, the oligosaccharide may be a disaccharide in which two monosaccharides are bonded, a trisaccharide in which three monosaccharides are bonded, a tetrasaccharide in which four monosaccharides are bonded, or the like. The disaccharide in one or a plurality of embodiments may be maltose, sucrose, or the like. As a sugar, in particular, from the viewpoint of enhancing measurement sensitivity when a measurement is carried out at low temperatures, dextran, and maltose are preferable, and from the viewpoint of enhancing measurement sensitivity when a measurement is carried out at low temperatures and when a sample has a high lactate concentration, dextran is more preferable. A lactate sensor having a dextran-containing reagent layer can demonstrate more enhanced measurement sensitivity even when a sample has a high lactate concentration or even when the ambient temperature during measurement is low, and is thus useful in, for example, winter sports training. Dextran is not particularly limited, and in one or a plurality of embodiments, known dextran that is used as a thickener can be used. The molecular weight of dextran is not particularly limited, and in one or a plurality of embodiments, it is 100 to 2000 and, from the viewpoint of solubility, preferably 1000 to 20000. From the viewpoint of productivity (cost) and detection sensitivity, the content of dextran per one lactate sensor is preferably 0.1 to 10 μg, 0.5 to 5.0 μg, or 1.0 to 3 μg. Herein, the phrase "measurement at low temperatures" in one or a plurality of embodiments means that the upper limit of the ambient temperature when carrying out a measurement using the lactate sensor is 10° C. or less or 5° C. or less, and the lower limit is −5° C. or more, 0° C. or more, or 1° C. or more.

From the viewpoint of enhancing measurement sensitivity, the reagent layer in one or a plurality of embodiments may further contain, for example, a layered inorganic compound and/or a surfactant. The layered inorganic compound is not particularly limited, and layered inorganic compounds that are use in conventional biosensors or biosensors that may be developed in the future can be used, and from the same viewpoint, swelling clay minerals having ion exchangeability are preferable. Among swelling clay minerals, from the same viewpoint, bentonite, smectite, vermiculite, synthetic fluorine mica, and the like are preferable, and synthetic smectite such as synthetic hectorite and synthetic saponite, swelling synthetic mica such as synthetic fluorine mica, synthetic mica such as sodium mica (natural micas are usually non-swelling clay minerals), and the like are more preferable. These layered inorganic compounds may be used singly, and two or more may be used as a combination.

The surfactant is not particularly limited, and surfactants that are used in conventional biosensors or biosensors that may be developed in the future can be used, and nonionic, anionic, cationic, or ampholytic surfactants are suitably usable. Among these surfactants, from the viewpoint of enhancing measurement sensitivity, ampholytic surfactants are preferable. Ampholytic surfactants in one or a plurality of embodiments may be carboxybetaine, sulfobetaine, phosphobetaine, and the like, and from the same viewpoint, sulfobetaine is preferable. Sulfobetaine in one or a plurality of embodiments may be CHAPS (3-[(3-cholamidopropyl)dimethylammonio]propanesulfonate), CHAPSO (3-[(3-cholamidopropyl)dimethylammonio]-2-hydroxy-1-propanesulfonate), alkyl hydroxy sulfobetaine, or the like, and CHAPS is preferable from the same viewpoint.

The reagent layer may have a single-layer structure in which all reagents are contained or may be a laminar structure composed of a multi-layer structure. In one or a plurality of embodiments, the reagent layer may have a configuration created by forming a first reagent layer containing a mediator and forming thereon a second reagent layer containing lactate oxidase and ACES. Also, in one or a plurality of embodiments where a ruthenium compound and PMS are used in combination as mediators, the reagent layer may have a configuration created by forming a first reagent layer containing a ruthenium compound and forming thereon a second reagent layer containing lactate oxidase, ACES, and PMS. When the reagent layer contains a sugar such as a polysaccharide, it is preferable that the second reagent layer contains a sugar such as a polysaccharide. From the viewpoint of storage stability, the reagent layer of the lactate sensor is preferably disposed in a dry state on the electrode system.

The size of the lactate sensor of the present disclosure is not particularly limited and can be suitably set in accordance with, for example, the amount of a sample to be supplied, and in one or a plurality of embodiments, the overall length may be 5 to 50 mm, the overall width may be 1 to 50 mm, the maximum thickness may be 2000 to 500 μm, and the minimum thickness may be 50 to 500 μm. Note that the term "length" refers to the length in the longitudinal direction of the lactate sensor, and the term "width" refers to the length in the width direction of the lactate sensor.

In one or a plurality of embodiments, the lactate sensor of the present disclosure may be used in combination with a measurement instrument, provided with various means such as a means for applying a predetermined voltage for a specific duration, a means for measuring an electrical signal transmitted from the lactate sensor, and a calculating means for converting the electrical signal into the concentration of a measurement target.

[Method for Producing Lactate Sensor]

Still another aspect of the present disclosure relates to a method for producing a lactate sensor including forming a reagent layer containing lactate oxidase, a mediator, and ACES on an electrode system provided on an insulating substrate, the electrode system including at least a working electrode and a counter electrode. According to the production method of the present disclosure, the lactate sensor of the present disclosure can be produced. The same lactate oxidase, mediator, and ACES as those of the lactate sensor of the present disclosure can be used.

In one or a plurality of embodiments, the reagent layer may be formed by disposing a reagent solution on the electrode system. The content of ACES in the reagent solution in one or a plurality of embodiments from the viewpoint of shortening the measurement time and enhancing measurement sensitivity is, for example, 0.1 to 10 wt % or 0.5 to 5.0 wt %. The content of lactate oxidase in the reagent solution from the viewpoint of productivity (cost) and detection sensitivity is, for example, 0.5 to 10 kU/mL or 1 to 5 U/mL.

In another embodiment of the production method of the present disclosure, from the viewpoint of shortening the measurement time and enhancing measurement sensitivity, the mediator is preferably a ruthenium compound or a combination of a ruthenium compound and phenazine methosulfate or a derivative thereof. The content of ruthenium compound per a reagent solution in one or a plurality of embodiments from the viewpoint of productivity (cost) and detection sensitivity is, for example, 1.0 to 15 wt % or 5.0 to 10 wt %. The content of PMS per a reagent solution from the viewpoint of productivity (cost) and detection sensitivity is, for example, 10 to 1000 pmol or 100 to 500 pmol.

In another embodiment of the production method of the present disclosure, from the viewpoint of producing a lactate sensor with enhanced measurement sensitivity, it is preferable that the reagent solution contains a sugar such as a polysaccharide, and from the viewpoint of producing a lactate sensor demonstrating enhanced measurement sensitivity even when a measurement is carried, out at low temperatures and even when a sample has a high lactate concentration, it is more preferable that the reagent solution contains dextran. As dextran, the same dextran as that described for the foregoing lactate sensor of the present disclosure can be used. The content of dextran per a reagent solution in one or a plurality of embodiments from the viewpoint of productivity (cost) and detection sensitivity is, for example, 0.01 to 1 wt % or 0.05 to 0.1 wt %.

In another embodiment of the production method of the present disclosure, the reagent may further contain a layered inorganic compound and/or a surfactant. In one or a plurality of embodiments, the same layered, inorganic compound and surfactant as those described for the foregoing lactate sensor of the present disclosure can be used.

In another embodiment of the production method of the present disclosure, formation of the reagent layer may be achieved by, for example, forming a first reagent layer by disposing a first reagent solution containing a ruthenium compound on the electrode system and forming a second reagent layer by disposing a second reagent solution containing lactate oxidase, PMS, and ACES on the first reagent layer. In this case, it is preferable that the first reagent solution further contains a layered inorganic compound and/or a surfactant and the second reagent solution further contains a sugar such as a polysaccharide.

The content of ruthenium compound in the first reagent solution in one or a plurality of embodiments from the viewpoint of productivity (cost) and detection sensitivity is, for example, 0.05 to 1.0 wt % or 0.1 to 0.5 wt %. The content of ACES in the second reagent solution in one or a plurality of embodiments from the viewpoint of shortening the measurement time and enhancing measurement sensitivity is, for example, 0.1 to wt % or 0.5 to 5.0 wt %. The content of PMS in the second reagent solution in one or a plurality of embodiments from the viewpoint of productivity (cost) and detection sensitivity is, for example, 10 to 1000 pmol or 100 to 500 pmol. The content of lactate oxidase in the second reagent solution in one or a plurality of embodiments from the viewpoint of productivity (cost) and detection sensitivity is, for example, 0.5 to 1.0 kU/mL or 1 to 5 U/mL.

[Method for Measuring Lactate Concentration]

Another aspect of the present disclosure relates to a method for measuring a lactate concentration including bringing a sample into contact with a reagent containing lactate oxidase and ACES, and electrochemically measuring a reaction between lactate in the sample and the lactate oxidase via a mediator. According to the lactate concentration measurement method of the present disclosure, a time needed for the reaction can be shortened, thus making it possible to carry out a measurement in a short period of time, and it is thus possible to accurately measure the lactate concentration in a short period of time preferably even when the sample has a high lactate concentration. One embodiment of the lactate concentration measurement method of the present disclosure is a lactate concentration measurement method that uses the lactate sensor of the present disclosure.

Herein, the phrase "electrochemically measuring" means that a measurement is carried out using an electrochemical measurement technique, and in one or a plurality of embodiments, the electrochemical measurement technique may be amperometry, potentiometry, coulometry, or the like. Above all, a method that measures by amperometry the current generated when a reduced electron carrier is oxidized by voltage application is particularly preferable.

In another embodiment, the lactate concentration measurement method of the present disclosure may include applying voltage to the electrode system after the sample is brought into contact with the reagent, measuring the value of a response current discharged when the voltage is applied, and calculating the lactate concentration in the sample based on the value of a response current. The applied voltage is not particularly limited, and the voltage, applied in one or a plurality of embodiments is preferably 10 to 700 mV, 50 to 500 mV, or 100 to 400 mV.

In another embodiment, the lactate concentration measurement method of the present disclosure may apply voltage to the electrode system after retaining the electrode system without voltage application for a predetermined period of time after the sample is brought into contact with the reagent, or may apply voltage to the electrode system simultaneously with the contact between the sample and the reagent. The duration of retaining the electrode system without voltage application in one or a plurality of embodiments is greater than 0 seconds and equal to or less than 30 seconds, or more than 0 seconds and equal to or less than 10 seconds.

Regarding the lactate concentration measurement method of the present disclosure, application of voltage to the electrode system, measurement of the value of a response current, and calculation of the lactate concentration can be suitably performed with, for example, as conventional lactate concentration measurement device or a lactate concentration measurement device that may be developed in the future.

[Lactate Concentration Measurement System]

Another aspect of the present disclosure relates to a lactate concentration measurement system for measuring the lactate concentration in it sample, including the lactate sensor of the present disclosure, a means for applying voltage to an electrode system of the lactate sensor, and a means for measuring a current in the electrode system. The lactate concentration measurement system of the present disclosure measures the lactate concentration in a sample using the lactate sensor of the present disclosure, and therefore the time needed for the reaction is short, thus making it possible to carry out the measurement in a short period of time. The lactate concentration measurement system of the present disclosure in one or a plurality of embodiments even where the sample has a high lactate concentration or the ambient temperature is low can accurately measure the lactate concentration in a short period of time.

As long as the application means can be in conduction with the electrode system of the lactate sensor and apply voltage, the application means is not particularly limited and a known application means can be used. The application means in one or a plurality of embodiments can include, a contactor that can be brought into contact with the electrode system of the lactate sensor, a power source such as a DC power source, and the like.

The measurement means measures the current in the electrode system generated when voltage is applied, and in one or a plurality of embodiments, it is sufficient that the measurement means is capable of measuring the value of a response current that correlates with the amount of electrons discharged from the mediator in the reagent layer of the lactate sensor, and conventional measurement means and measurement means that may be developed in the future can be used.

Figure 1:
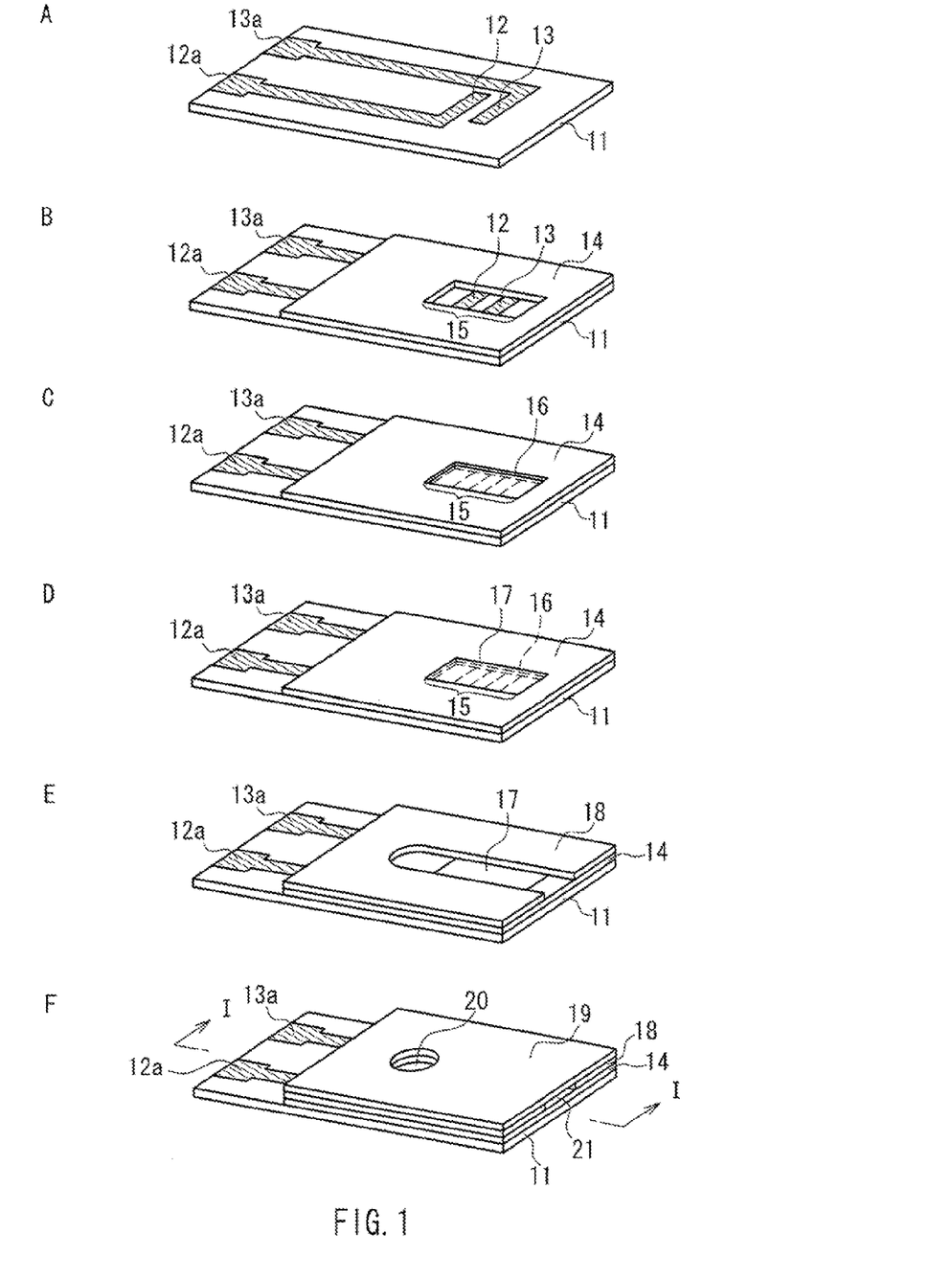
FIG. 1 is a schematic explanatory diagram of one example of a method for producing a lactate sensor.
Figure 2:
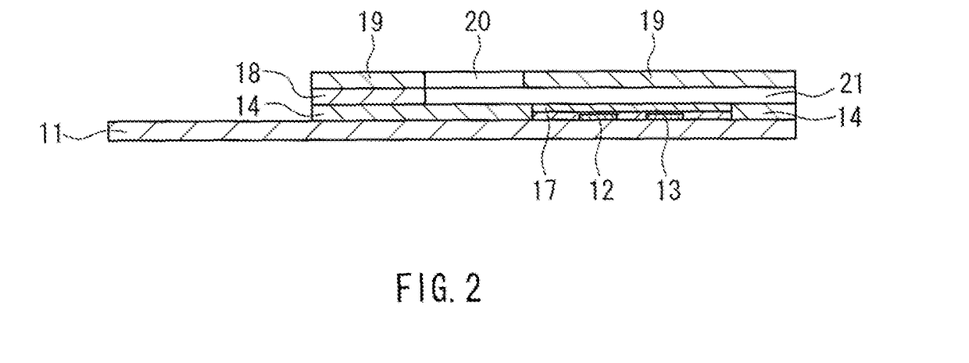
FIG. 2 is a schematic explanatory diagram of one example of a configuration of a lactate sensor, and is a cross-sectional diagram taken along the line I-I of the lactate sensor shown in FIG. 1F.

One embodiment of the lactate sensor and the production method of the present disclosure will now be described in reference to FIGS. 1 and 2. FIGS. 1A to 1F are perspective diagrams showing a series of steps of producing the lactate sensor of this embodiment. FIG. 2 is a cross-sectional diagram taken along the line I-I of the lactate sensor shown in FIG. 1F. In FIGS. 1A to 1F and FIG. 2, the same components are given the same reference numerals. Note that the following description is merely an example, and the present disclosure is not limited thereto.

As shown in FIGS. 1F and 2, the lactate sensor includes an insulating substrate 11, an electrode system configured with a working electrode 12 having a lead 12a and a counter electrode 13 having a lead 13a, an insulating layer 14, it first reagent layer 16, a second reagent layer 17, a spacer 18 having an opening, and a cover 19 having a through-hole 20. The electrode system is formed on the insulating substrate 11. The insulating layer 14 is thrilled on the insulating substrate 11 but not on the portion that is an upper part of the electrode system and where the leads 12a, 13b of the electrode system and the first reagent layer 16, which will be described below, are formed. The first reagent layer 16 and the second reagent layer 17 are formed in this order on the working electrode 12 and the counter electrode 13 and on the portion where the insulating layer 14 is not formed. The portion where the first reagent layer 16 and the second reagent layer 17 are formed serves as a detecting part 15. The spacer 18 is provided on the insulating layer 14 and has an opening that corresponds to the second reagent layer 17 and the through-hole 20 of the cover 19. The cover 19 is provided on the spacer 18. As shown in FIG. 1B, in the lactate sensor, the opening of the spacer 18, which is sandwiched by the second reagent layer 17, the insulating layer 14, and the cover 19, serves as a sample supply part 21 that has a capillary structure, and the through-hole 20 of the cover 19 serves as an air hole for drawing in a sample by capillary action.

The material of the insulating layer 14 in one or a plurality of embodiments may be an insulating resin. The insulating resin in one or a plurality of embodiments may be polyester butyral resin, phenol resin, or the like. The material of the spacer 18 in one or a plurality of embodiments may be resin film, tape, or the like. The material of the cover 19 is not particularly limited, and in one or a plurality of embodiments, various plastics can be used, with transparent resins being preferable, and PET being more preferable.

The reagent configuration, i.e., what is contained in the first reagent layer 16 and what is contained in the second reagent layer 17, is not particularly limited, and in one or a plurality of embodiments, a configuration in which the first reagent layer 16 contains a ruthenium compound and a layered inorganic compound and the second reagent layer 17 contains lactate oxidase, PMS, a surfactant, and ACES may be used.

The lactate sensor of this embodiment can be produced, for example, as follows.

First, as shown in FIG. 1A, the insulating substrate 11 on which an electrode system composed of the working electrode 12 having the lead 12a and the counter electrode 13 having the lead 13a is formed is provided. A commercially available insulating substrate on which an electrode system has been formed may be used, or an electrode system may be formed on the insulating substrate 11. The material of the insulating substrate, the material of the electrodes, and the method for forming the electrodes are as described above.

Next, as shown in FIG. 1B, the insulating layer 14 is formed on the insulating substrate 11 on which the electrode system is formed. The insulating layer 14 in one or a plurality of embodiments can be formed by printing on the insulating substrate 11 an insulating paste in which an insulating resin is dissolved in a solvent, and then subjecting the insulating substrate 11 to a heat or UV treatment. The solvent in one or a plurality of embodiments may be carbitol acetate, a dibasic acid ester-based mixed solvent (DBE solvent), or the like.

Next, as shown in FIGS. 1E and 1D, the first reagent layer 16 and the second reagent layer 17 are formed in this order on the electrode system and the insulating substrate 11 in the detecting part 15 where the insulating layer 14 is not formed. The first reagent layer 16 and the second reagent layer 17 can be formed by dispensing reagent solutions that contain reagents to be accommodated in the respective layers, and drying the solutions. The concentrations of the reagent solutions are as described above.

Next, as shown in FIGS. 1E and 1F, the spacer 18 and the cover 19 are disposed in this order on the insulating layer 14.

An example of a lactate measurement method that uses the lactate sensor of this embodiment will now be described. Note that the following description is merely an example, and the present disclosure is not limited thereto.

First, a whole blood sample is brought into contact with one end of the sample supply part. 21 of the lactate sensor. The sample supply part 21 has a capillary structure as stated above, and the opening 20 of the cover 19 that corresponds to the other end of the sample supply part 21 serves as an air hole, and therefore the sample is drawn in to the lactate sensor by capillary action. The sample that has been drawn in permeates the second reagent layer 17 and dissolves lactate oxidase, ACES, and the like present in the second reagent layer 17, and reaches the surface of the first reagent layer 18, which is a layer located under the second reagent layer 17. Then, lactate in the sample, lactate oxidase and PMS that have reached the surface and a ruthenium compound react in the presence of ACES. Specifically; lactate, which is a measurement target, is oxidized by lactate oxidase, electrons migrated due to the oxidation reaction are transferred to the ruthenium compound via PMS, and thus a reduced ruthenium al complex is formed. Then, electrons are transferred between the reduced ruthenium (H) complex and the electrode system located below the first reagent layer 18, thus making it possible to measure the lactate concentration.

The present disclosure may relate to one or a plurality of the following aspects:

[1] A lactate sensor comprising an insulating substrate, an electrode system including at least a working electrode and a counter electrode provided on the substrate, and a reagent layer provided on the electrode system, wherein the reagent layer contains lactate oxidase, a mediator, and N-(2-acetamide)-2-aminoethanesulfonic acid.

[2] The lactate sensor according to [1], wherein the reagent layer further contains a sugar selected from the group consisting of oligosaccharides and polysaccharides.

[3] The lactate sensor according to [2], wherein the sugar is dextran or maltose, preferably dextran.

[4] The lactate sensor according to any of [1] to [3], wherein the reagent layer further contains a layered inorganic compound and/or a surfactant.

[5] The lactate sensor according to any of [1] to [4], wherein the mediator is selected from the group consisting of potassium ferricyanide, cytochrome C, pyrroloquinoline quinone, NAD+, NADP+, copper complexes, ruthenium compounds, and phenazine methosulfate and derivatives thereof.

[6] The lactate sensor according to [5], wherein the mediator is a ruthenium compound, or a ruthenium compound and phenazine methosulfate or a derivative thereof.

[7] The lactate sensor according to [5] or [6], wherein the phenazine methosulfate derivative is 1-methoxy-5-methyl phenazinium methyl sulfate.

[8] A method for measuring a lactate concentration, comprising:
  bringing a sample into contact with a reagent containing lactate oxidase and N-(2-acetamide)-2-aminoethanesulfonic acid, and
  electrochemically measuring a reaction between lactate in the sample and the lactate oxidase via a mediator.

[9] The measurement method according to [8], wherein the reagent further contains a sugar selected from the group consisting of oligosaccharides and polysaccharides.

[10] The measurement method according to [9], wherein the sugar is dextran or maltose, preferably dextran.

[11] The measurement method according to any of [8] to [10], carried out using the lactate sensor of any of [1] to [7].

[12] The measurement method according to any of [8] to [11], comprising:
  applying voltage to the electrode system after the contact,
  measuring a value of a response current discharged when the voltage is applied, and
  calculating a lactate concentration in the sample based on the value of a response current.

[13] A method for producing a lactate sensor, the method comprising forming a reagent layer containing lactate oxidase, a mediator, and N-(2-acetamide)-2-aminoethanesulfonic acid on an electrode system provided on an insulating substrate, the electrode system including at least a working electrode and a counter electrode.

[14] The production method according to [13], wherein the reagent layer further contains a sugar selected from the group consisting of oligosaccharides and polysaccharides.

[15] The production method according to [14], wherein the sugar is dextran or maltose, preferably dextran.

[16] A lactate concentration measurement system for measuring a lactate concentration in a sample, the system comprising:
  the lactate sensor of any of claims [1] to [7],
  a means for applying voltage to the electrode system of the lactate sensor, and
  a means for measuring a current in the electrode system.

Below, the present disclosure is further described using examples and comparative examples. Note that the present disclosure should not be construed as being limited to the examples.

EXAMPLES

Example 1

The lactate sensor of Example 1 having the same structure as the lactate sensor shown in FIG. 1 was prepared in the following manner.

First, a PET substrate (having a length of 50 mm, a width of 6 mm, and a thickness of 250 μm) was provided, as an insulating substrate 11 of a lactate sensor, and a carbon electrode system composed of a working electrode 12 and a counter electrode 13 having a lead 12a and a lead 13a, respectively, was formed by screen printing on one surface of the substrate.

Next, an insulating layer 14 was farmed on the electrode system as described below. First, an insulating paste was prepared by dissolving a polyester insulating resin in a carbitol acetate solvent so as to reach a concentration of 75 wt %, and the paste was scram-printed on the electrode system. Printing conditions included a 300 mesh screen, a squeegee pressure of 40 kg, and a printing amount of 0.002 mL/cm$^2$ of the electrode area. Screen-printing was not performed on a detecting part 15 or the leads 12a, 13a. Then, the insulating paste was heat-treated at 90° C. for 60 minutes, and thus an insulating layer 14 was formed.

Next, a first reagent layer 16 was formed on the detecting part 15 on which the insulating layer 14 was not formed. First, a first reagent solution (pH 7.5) containing 0.3 wt % of synthetic smectite (trade name "Lucentite SWN", manufactured by CO-OP Chemical), 6.0 wt % of a ruthenium compound ([Ru(NH$_3$)$_6$]Cl$_3$, manufactured by Dojindo Laboratories), sodium acetate, and succinic acid was prepared. 1.0 μL of the first reagent solution was dispensed to the detecting part 15. The surface area of the detecting part 15 was about 0.1 cm$^2$, and the surface area of the working electrode 12 and the counter electrode 13 in the detecting part 15 was about 0.12 cm$^2$. Then, the first reagent solution was dried at 30° C., thus forming the first reagent layer 16.

Furthermore, a second reagent layer 17 was formed an the first reagent layer 16. First, a second reagent solution containing 2 U of lactate oxidase (trade name "LCO-301", manufactured by Toyobo Co., Ltd.), 25 wt % of 1-methoxy PMS (manufactured by Dojindo Laboratories), an ACES buffer solution (pH 7.5), and a surfactant was prepared. 1.0 μL of the second reagent solution was dispensed to the first reagent layer 16 and dried at 30° C., thus forming the second reagent layer 17.

Finally, a spacer 18 having an opening was provided on the insulating layer 14, and a cover 19 having a through-hole 20 that serves as an air hole was provided on the spacer 18, and thus the lactate sensor of Example 1 was prepared. The aperture of the opening of the spacer 18 sandwiched between the cover 19 and the insulating layer 14 was regarded as a sample supply part 21.

Comparative Examples 1 to 6

For Comparative Examples 1 to 6, lactate sensors were prepared in the same manner as in Examples 1 except that buffers shown in Table 1 below were used in place of ACES.

Lactate sensors of Example 1 and Comparative Examples 1 to 6 were used to measure lactate in a sample. 2 mmol/L, of a lactate preparation was used as a sample, and a lactate measurement jig was used as a measurement device. Measurement was carried out as follows. In an environmental examination room that was set at 25° C., a sample was supplied to a lactate sensor, then, after analyte detection, no voltage was applied for 10 seconds followed by a voltage of 200 mV for 5 seconds. Results are shown in Table 1 and in the graph of FIG. 3.

TABLE 1

|  | Buffer | Current (μA) |
|---|---|---|
| Ex. 1 | ACES | 0.091 |
| Comp. Ex. 1 | Tris | 0.009 |

TABLE 1-continued

|  | Buffer | Current (μA) |
| --- | --- | --- |
| Comp. Ex. 2 | MOPSO | 0.002 |
| Comp. Ex. 3 | TES | 0.015 |
| Comp. Ex. 4 | Bis tris | 0.011 |
| Comp. Ex. 5 | MOPS | 0.006 |
| Comp. Ex. 6 | MES | 0.017 |

Figure 3:
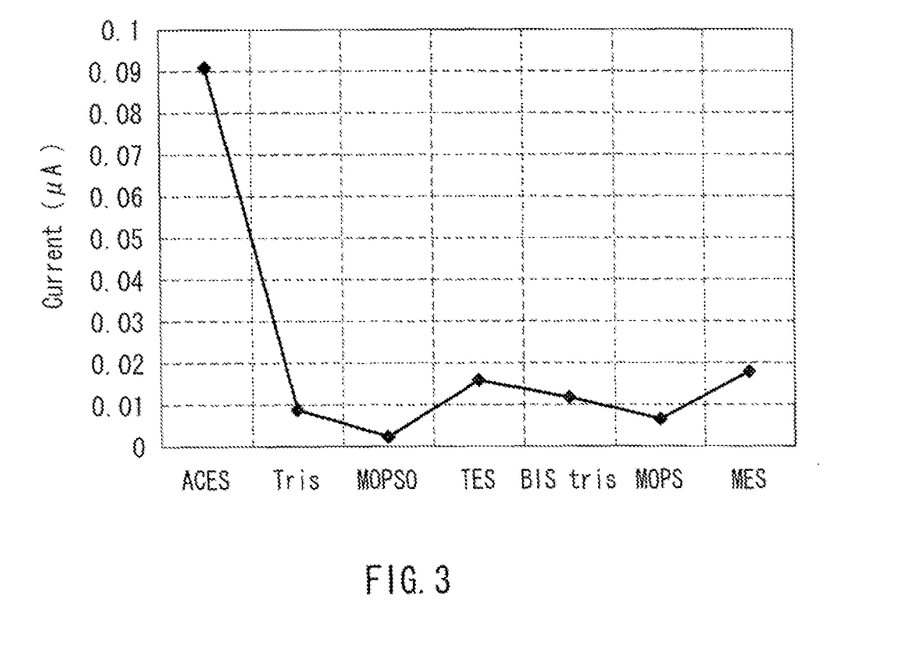
FIG. 3 is one example of a graph indicating a current detected when a sample is measured with the lactate sensors of Example 1 and Comparative Examples 1 to 6.

As shown in Table 1 and FIG. 3, the lactate sensor of Example 1 compared with the lactate sensors of Comparative Examples 1 to 6 detected a sufficient response current. Also, it was confirmed that the lactate sensor of Example 1 enables a measurement in a very short measurement time of 5 seconds after detection of a spot of the analyte.

Example 2

Figure 4:
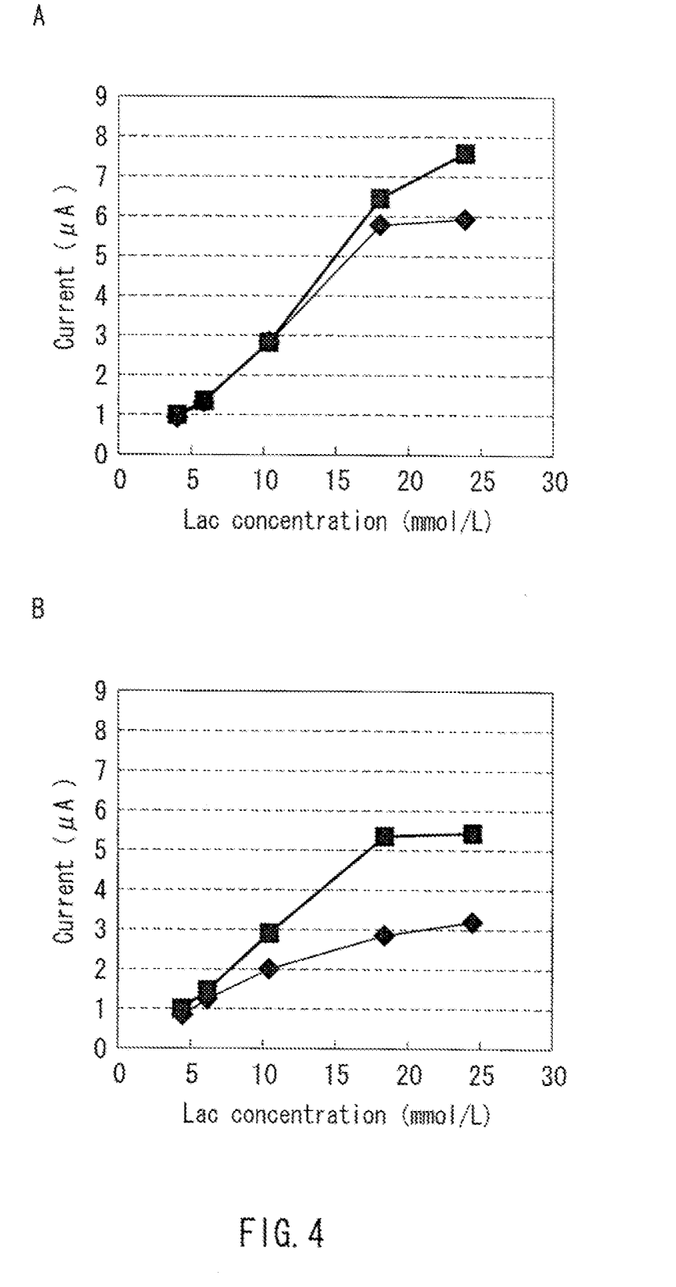
FIG. 4 shows examples of graphs indicating the relationship between the current and the lactate concentration of a sample detected when the sample is measured with the lactate sensors of Examples and 2.

A lactate sensor was prepared in the same manner as in Example 1 except that the second reagent solution contained 0.5 wt % of dextran (a molecular weight of 5000 to 10000, trade name "dextran", Nacalai Tesque, Inc.). Lactate was measured in the same manner as in Example 1 except that the lactate sensors of Examples 1 and 2 were used, venous whole blood samples with adjusted lactate concentrations (lactate concentrations of 4, 6, 10, 18, and 24 mg/dL) were used, and the measurement temperature was 25° C. or 10° C. Results are shown in FIG. 4. FIG. 4A is a graph showing the results obtained at a measurement temperature of 25° C. and FIG. 4B is a graph showing the results obtained at a measurement temperature of 10° C. In FIGS. 4A and 4B, squares represent data for the lactate sensor of Example 1, and rhombuses represent data for the lactate sensor of Example 2.

It was confirmed that the lactate sensors of Examples 1 and 2 both enable a measurement in a very short measurement time of 5 seconds after detection of a spot of the analyte. Also, it was confirmed that, as shown in the graph of FIG. 4A, the dextran-containing lactate sensor of Example 2 enables a more accurate measurement in a short reaction time (10 seconds after detection of a spot of the analyte) even when the lactate concentration is high (for example, a concentration exceeding 10 mmol/L, preferably a concentration exceeding 18 mmol/L). Also, it was confirmed that, as shown in the graph of FIG. 4B, the dextran-containing lactate sensor of Example 2 enables a more accurate measurement in a short reaction time (10 seconds after detection of a spot of the analyte) even when the measurement temperature is as low as 10° C. Also, it was confirmed from the same measurement carried out using the lactate sensor of Example 2 at a measurement temperature of 5° C. or 0° C. that a more accurate measurement can be achieved in a short reaction time (10 seconds after detection of a spot of the analyte), as in the measurement carried out at 10° C. (data not shown).

Example 3

Lactate sensors were prepared in the same manner as in Example 2 except that the molecular weight of the dextran used was 100 to 500, 1000 to 2000, or 10000 to 20000, and lactate was measured using these sensors. The same results as those obtained from the lactate sensor of Example 2 in which dextran having a molecular weight of 5000 to 10000 was used were obtained (data not shown).

Comparative Example 7

A lactate sensor was prepared in the same manner as in Example 2 except that a disodium hydrogen phosphate buffer solution was used in place of the ACE buffer solution in the second reagent solution.

Figure 5:
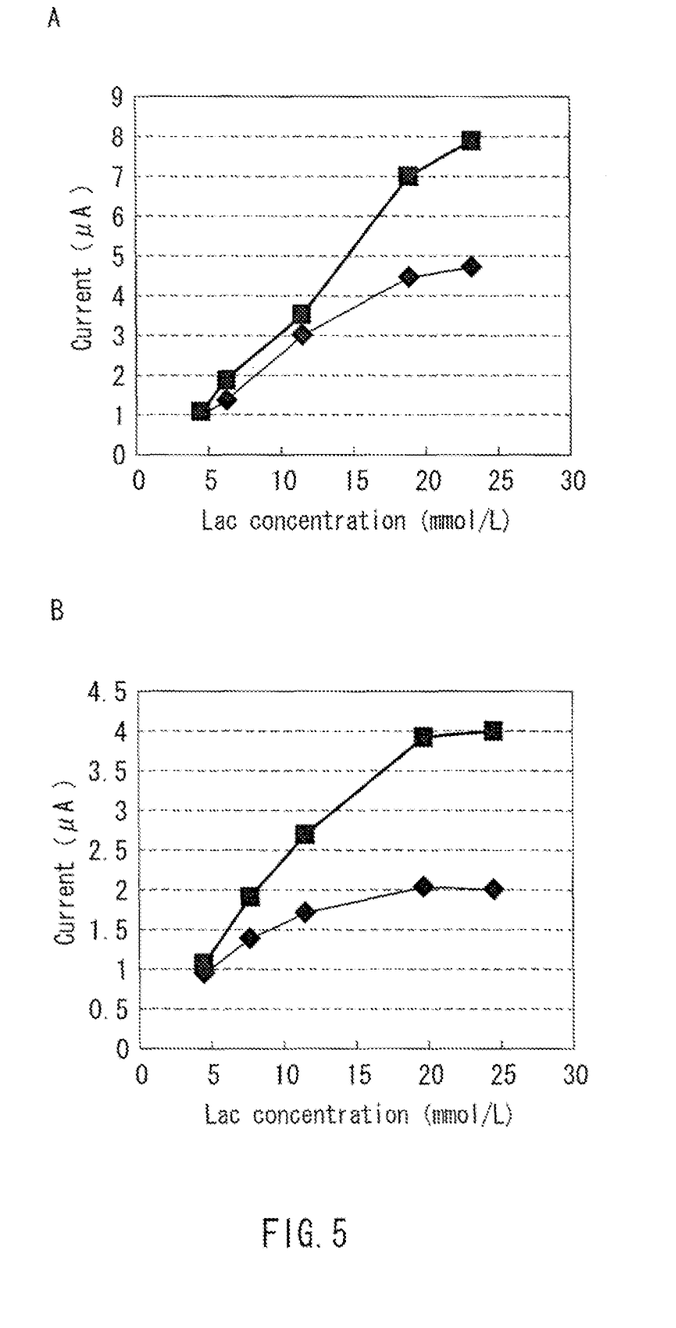
FIG. 5 shows examples of graphs indicating the relationship between the current and the lactate concentration of a sample detected when the sample was measured with the lactate sensors of Example 2 and Comparative Example 7.

Lactate was measured in the same manner as in Example 2 using the lactate sensors of Example 2 and Comparative Example 7. Results are shown in the graphs of FIG. 5.

FIG. 5A is a graph showing the results obtained at a measurement temperature of 25° C., and FIG. 5B is a graph showing the results obtained at a measurement temperature of 10° C. In FIGS. 5A and 5B, squares represent data for the lactate sensor of Example 2, and rhombuses represent data for the lactate sensor of Comparative Example 7. As shown in FIGS. 5A and 5B, the results showed that the lactate sensor of Comparative Example 7 in which disodium hydrogen phosphate was used as a buffer failed to detect a sufficient current at measurement temperatures of both 25° C. and 10° C., and 10 seconds after analyte detection is not a sufficient reaction time. In contrast, it was confirmed that the lactate sensor of Example 2 detected a sufficient current at measurement temperatures of both 25° C. and 10° C. and enables an accurate measurement in a short reaction time.

Example 4

Lactate sensors were prepared in the same manner as in Example 1 except that, the second reagent solution contained 0.5 wt % of dextran molecular weight of 50000 to 70000, trade name "Dextran", Nacalai Tesque, Inc.), 0.5 wt % of cyclodextrin (a molecular weight of 1134.98, trade name "β-Cyclodextrin", Nacalai Tesque, Inc.), or 0.5 wt % of maltose (a molecular weight of 360.31, trade name "Maltose monohydrate", Nacalai Tesque, Inc). Lactate was measured in the same manner as in Example 1 except that the resulting lactate sensors were used, venous whole blood samples with adjusted lactate concentrations (lactate concentrations of 10 and 20 mg/dL) were used, and the measurement temperature was 10° C. For a reference, a measurement was carried out with a prototype having the same configuration as the lactate sensor of Example 1. Results are shown in FIG. 6.

Figure 6:
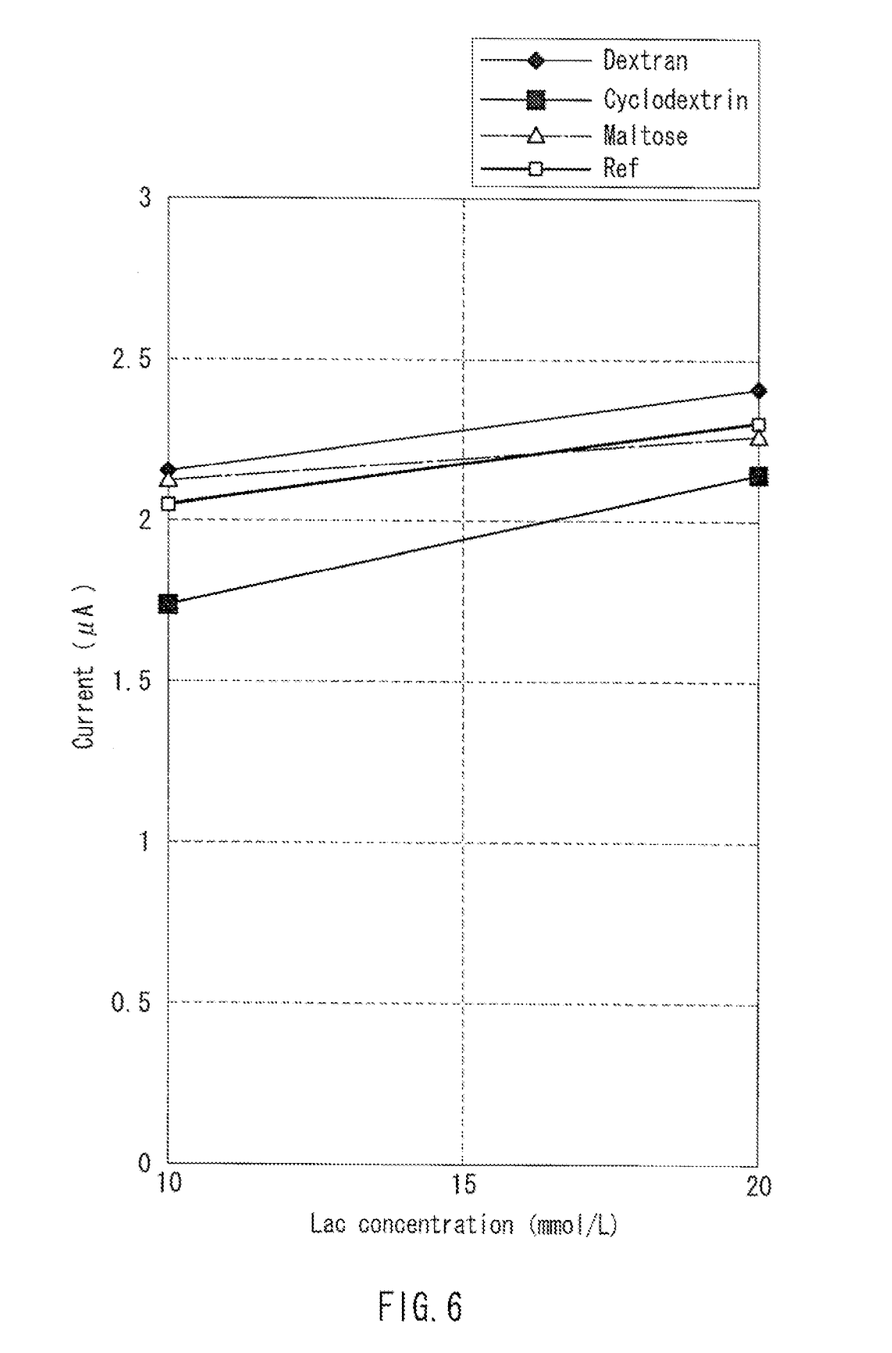
FIG. 6 shows examples of graphs indicating the relationship between the current and the lactate concentration of a sample detected when the sample was measured with the lactate sensors of Example 4.

In FIG. 6, rhombuses represent data for the dextran-containing lactate sensor, black squares represent data for the cyclodextrin-containing lactate sensor, triangles represent data for the maltose-containing lactate sensor, and white squares represent data for the reference. As shown in FIG. 6, with any lactate sensor, a sufficient current was detected both when the lactate concentration was low (10 mg/dL) and when high (20 mg/dL), and it was thus possible to perform an accurate measurement in a short reaction time. In particular, the maltose-containing lactate sensor showed excellent sensitivity at a low lactate concentration and enabled a highly accurate measurement, and the dextran-containing lactate sensor showed excellent sensitivity at both low and high lactate concentrations and enabled a very highly accurate measurement.

The present disclosure is useful in the medical field and/or the scientific field such as non-remedial medicine, biochemistry; and biology.

What is claimed is:

1. A lactate sensor comprising an insulating substrate, an electrode system including at least a working electrode and a counter electrode provided on the substrate, and a reagent layer provided on the electrode system,
wherein the reagent layer contains lactate oxidase, at least two mediators, and N-(2-acetamide)-2-aminoethane-sulfonic acid, and
wherein one of the at least two mediators contains a ruthenium compound, and the other mediator of the at least two mediators is a phenazine methosulfate and/or a derivative thereof.

2. The lactate sensor according to claim 1, wherein the reagent layer further contains a sugar selected from the group consisting of oligosaccharides and polysaccharides.

3. The lactate sensor according to claim 2, wherein the sugar is dextran.

4. The lactate sensor according to claim 1, wherein the reagent layer further contains a layered inorganic compound and/or a surfactant.

5. The lactate sensor according to claim 1, wherein the phenazine methosulfate derivative is 1-methoxy-5-methyl phenazinium methyl sulfate.

6. A lactate concentration measurement system for measuring a lactate concentration in a sample, the system comprising:
   the lactate sensor of claim 1,
   a means for applying voltage to the electrode system of the lactate sensor, and
   a means for measuring a current in the electrode system.

7. A method for measuring a lactate concentration, comprising:
   bringing a sample into contact with a reagent layer containing lactate oxidase and N-(2-acetamide)-2-aminoethanesulfonic acid, and
   electrochemically measuring a reaction between lactate in the sample and the lactate oxidase via at least two mediators, and
   wherein one of the at least two mediators contains a ruthenium compound, and the other mediator of the at least two mediators is a phenazine methosulfate and/or a derivative thereof.

8. The measurement method according to claim 7, carried out using the lactate sensor,
   wherein the lactate sensor comprises an insulating substrate, an electrode system including at least a working electrode and a counter electrode provided on the substrate, and a reagent layer provided on the electrode system,
   wherein the reagent layer contains lactate oxidase, at least two mediators, and N-(2-acetamide)-2-aminoethanesulfonic acid.

9. The measurement method according to claim 8, comprising:
   applying voltage to the electrode system after the contact,
   measuring a value of a response current discharged when the voltage is applied, and
   calculating a lactate concentration in the sample based on the value of a response current.

10. A method for producing a lactate sensor, the method comprising forming a reagent layer containing lactate oxidase, at least two mediators, and N-(2-acetamide)-2-aminoethanesulfonic acid on an electrode system provided on an insulating substrate, the electrode system including at least a working electrode and a counter electrode, and
    wherein one of the at least two mediators contains a ruthenium compound, and one other mediator of the at least two mediators is a phenazine methosulfate and/or a derivative thereof.

* * * * *